(12) United States Patent
Parrino et al.

(10) Patent No.: US 7,306,197 B2
(45) Date of Patent: Dec. 11, 2007

(54) CONNECTION ELEMENT AND CONNECTING DEVICE FOR TUBES

(75) Inventors: Andrea Parrino, Mirandola (IT); Guido Colli, Modena (IT)

(73) Assignee: Gambro Lundia AB, Lund (SE)

( * ) Notice: Subject to any disclaimer, the term of this patent is extended or adjusted under 35 U.S.C. 154(b) by 237 days.

(21) Appl. No.: 10/511,391

(22) PCT Filed: Mar. 21, 2003

(86) PCT No.: PCT/IB03/01055

§ 371 (c)(1),
(2), (4) Date: Oct. 15, 2004

(87) PCT Pub. No.: WO03/086528

PCT Pub. Date: Oct. 23, 2003

(65) Prior Publication Data

US 2005/0212292 A1 Sep. 29, 2005

(30) Foreign Application Priority Data

Apr. 18, 2002 (IT) .......................... MI2002A0819

(51) Int. Cl.
*F16K 51/00* (2006.01)
*F16L 29/00* (2006.01)
*F16L 37/28* (2006.01)

(52) U.S. Cl. .................... 251/149.6; 604/256
(58) Field of Classification Search ............ 251/149.1, 251/149.6, 149.7; 604/246, 256
See application file for complete search history.

(56) References Cited

U.S. PATENT DOCUMENTS 3,910,283 A 10/1975 Leveen
4,243,034 A 1/1981 Brandt
4,334,551 A 6/1982 Pfister
4,439,188 A 3/1984 Dennehey et al.
4,611,643 A 9/1986 Beebe et al.
4,638,668 A * 1/1987 Leverberg et al. ......... 73/866.5
4,645,494 A 2/1987 Lee et al.
4,655,762 A 4/1987 Rogers
4,745,950 A 5/1988 Mathieu
4,878,516 A 11/1989 Mathieu
5,122,123 A 6/1992 Vaillancourt
5,242,432 A 9/1993 DeFrank
5,349,984 A 9/1994 Weinheimer et al.
5,353,837 A 10/1994 Faust (Continued)

FOREIGN PATENT DOCUMENTS

EP 0 098 282 B1 1/1984

(Continued)

*Primary Examiner*—Eric Keasel
*Assistant Examiner*—John K. Fristoe, Jr.
(74) *Attorney, Agent, or Firm*—Finnegan, Henderson, Farabow, Garrett & Dunner, L.L.P.

(57) ABSTRACT

A description is given of a connecting device for tubes for medical use having a connection element (7) comprising a main body designed to be attachable to the end of a first tube, and a shut-off element made of an elastically deformable material and at least partly housed inside the main body, to allow or prevent, as required, fluid communication through the main body. The shut-off element has a longitudinal axis of symmetry and is designed to deform symmetrically. Also described are a tube and a peritoneal dialysis line using the connection element described above.

83 Claims, 6 Drawing Sheets

U.S. PATENT DOCUMENTS

| | | |
|---|---|---|
| 5,439,451 A | 8/1995 | Collinson et al. |
| 5,474,544 A | 12/1995 | Lynn |
| 5,501,426 A | 3/1996 | Atkinson et al. |
| 5,509,433 A | 4/1996 | Paradis |
| 5,555,908 A | 9/1996 | Edwards et al. |
| 5,569,235 A | 10/1996 | Ross et al. |
| 5,573,516 A | 11/1996 | Tyner |
| 5,676,346 A | 10/1997 | Leinsing |
| 5,699,821 A | 12/1997 | Paradis |
| 5,730,418 A | 3/1998 | Feith et al. |
| 5,733,270 A | 3/1998 | Ling et al. |
| 5,738,144 A | 4/1998 | Rogers |
| 5,743,892 A | 4/1998 | Loh et al. |
| 5,749,861 A | 5/1998 | Guala et al. |
| 5,782,808 A | 7/1998 | Folden |
| 5,782,816 A | 7/1998 | Werschmidt et al. |
| 5,788,215 A | 8/1998 | Ryan |
| 5,806,551 A | 9/1998 | Meloul et al. |
| 5,806,831 A | 9/1998 | Paradis |
| 5,839,715 A | 11/1998 | Leinsing |
| 5,957,898 A | 9/1999 | Jepson et al. |
| 5,967,410 A | 10/1999 | Lammers |
| 6,050,978 A * | 4/2000 | Orr et al. ............... 604/249 |
| 6,079,432 A * | 6/2000 | Paradis .................. 137/1 |
| 6,089,541 A | 7/2000 | Weinheimer et al. |
| 6,142,446 A | 11/2000 | Leinsing |
| 6,168,137 B1 | 1/2001 | Paradis |
| 6,206,861 B1 | 3/2001 | Mayer |
| 6,228,069 B1 | 5/2001 | Barth et al. |
| 6,234,538 B1 | 5/2001 | Lauer |
| 6,261,282 B1 | 7/2001 | Jepson et al. |
| 6,290,206 B1 | 9/2001 | Doyle |
| 6,299,131 B1 | 10/2001 | Ryan |
| 6,299,132 B1 | 10/2001 | Weinheimer et al. |
| 6,482,189 B2 | 11/2002 | Döpper et al. |
| 6,572,591 B2 | 6/2003 | Mayer |
| 6,581,906 B2 | 6/2003 | Pott et al. |
| 6,706,022 B1 | 3/2004 | Leinsing et al. |
| 2001/0016715 A1 | 8/2001 | Mayer |
| 2001/0042850 A1 | 11/2001 | Cote, Sr. et al. |
| 2002/0029020 A1 | 3/2002 | Cote, Sr. et al. |
| 2003/0032940 A1 | 2/2003 | Doyle |
| 2003/0060804 A1 | 3/2003 | Vaillancourt |
| 2003/0093061 A1 | 5/2003 | Ganem |
| 2003/0098430 A1 | 5/2003 | Leinsing et al. |
| 2003/0208165 A1 | 11/2003 | Christensen et al. |
| 2003/0209681 A1 | 11/2003 | Leinsing et al. |
| 2004/0073171 A1 | 4/2004 | Rogers et al. |
| 2004/0124388 A1 | 7/2004 | Kiehne |

FOREIGN PATENT DOCUMENTS

| | | |
|---|---|---|
| EP | 0 198 407 B1 | 10/1986 |
| EP | 0 327 850 B1 | 8/1989 |
| EP | 0 442 072 B1 | 8/1991 |
| EP | 0 472 088 A1 | 2/1992 |
| EP | 0 576 380 B1 | 12/1993 |
| EP | 0 715 860 B1 | 6/1996 |
| EP | 0 724 464 B1 | 8/1996 |
| EP | 0 478 365 B1 | 12/1996 |
| EP | 0 748 635 A2 | 12/1996 |
| EP | 0 766 572 B1 | 4/1997 |
| EP | 0 976 419 A1 | 2/2000 |
| EP | 1 004 329 B1 | 5/2000 |
| EP | 1 210 960 A1 | 6/2002 |
| EP | 1 236 482 B1 | 9/2002 |
| EP | 1 243 285 | 9/2002 |
| EP | 1 398 053 A1 | 3/2004 |
| JP | 2002-355318 | 12/2002 |
| JP | 2003-144546 | 5/2003 |
| WO | WO 96/30076 | 10/1996 |
| WO | WO 96/33762 | 10/1996 |
| WO | WO 97/24548 | 7/1997 |
| WO | WO 98/26835 | 6/1998 |
| WO | WO 98/50106 | 11/1998 |
| WO | WO 01/07102 A2 | 2/2001 |
| WO | WO 01/43814 A1 | 6/2001 |
| WO | WO 01/80928 A2 | 11/2001 |
| WO | WO 03/018104 | 3/2003 |
| WO | WO 03/030986 | 4/2003 |
| WO | WO 03/030987 | 4/2003 |
| WO | WO 2004/030744 A1 | 4/2004 |

* cited by examiner

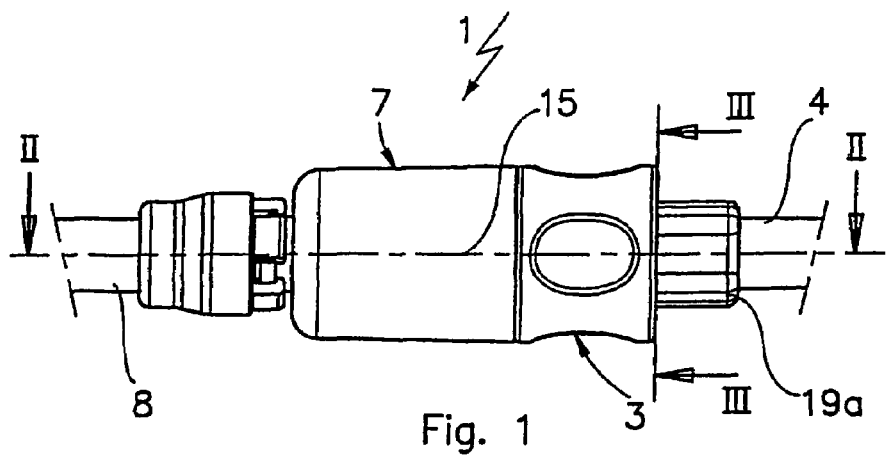
Fig. 1
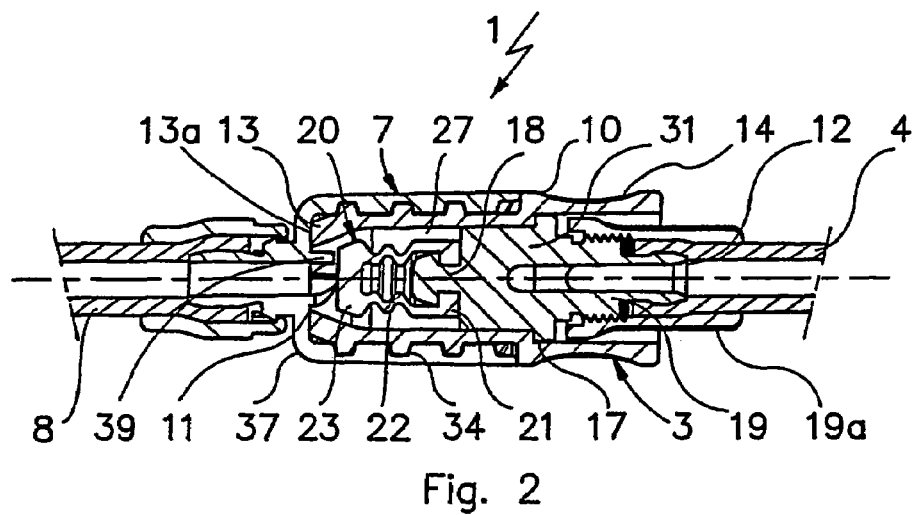
Fig. 2
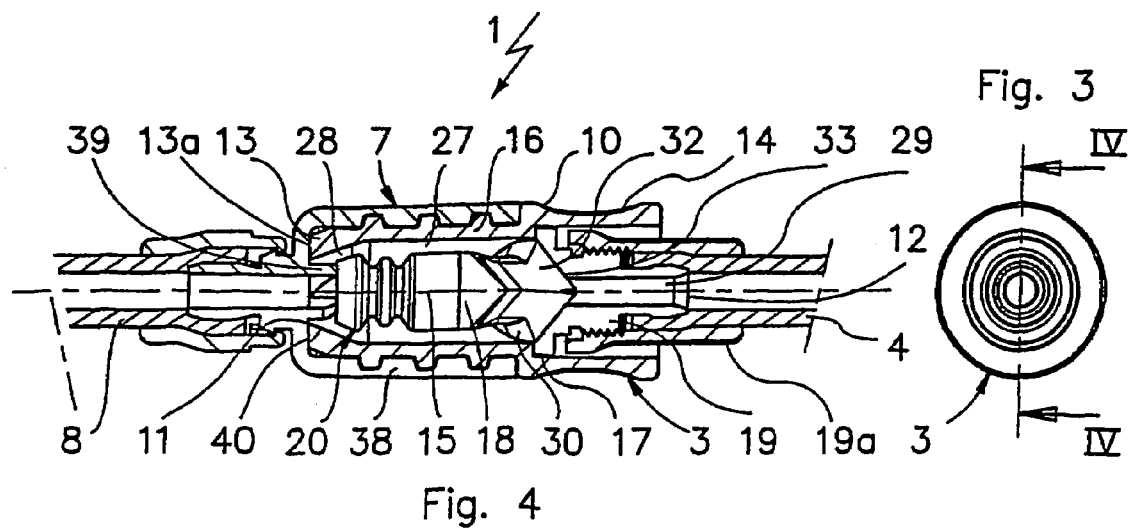
Fig. 3
Fig. 4

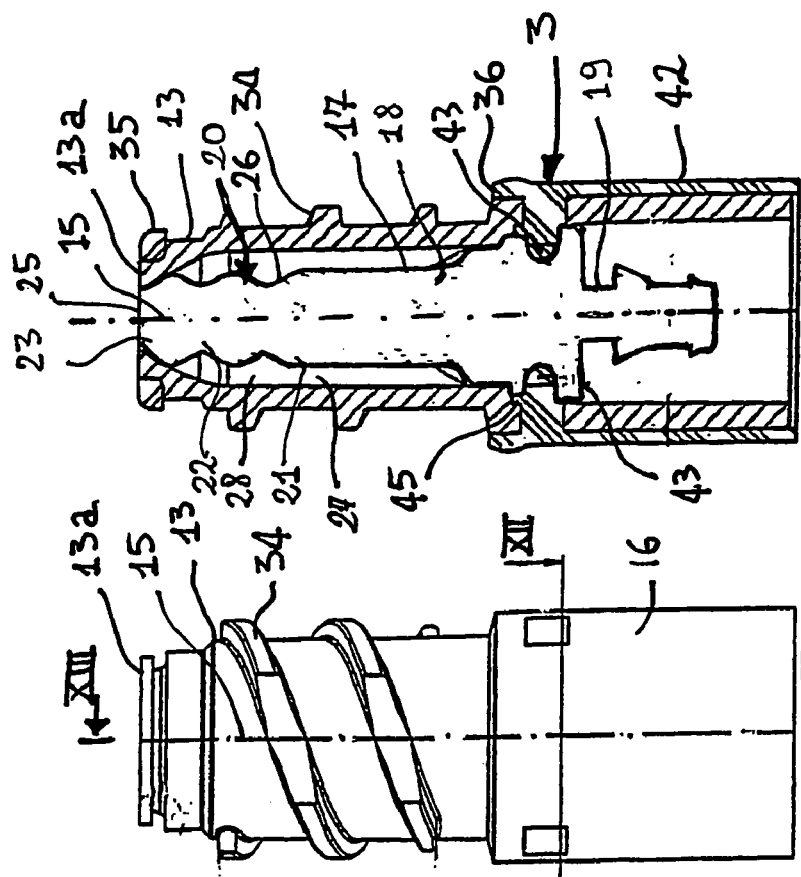
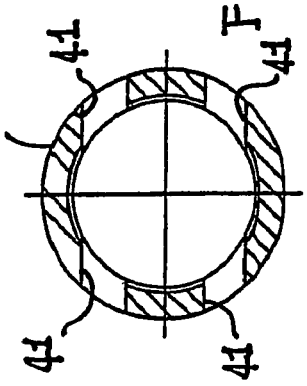
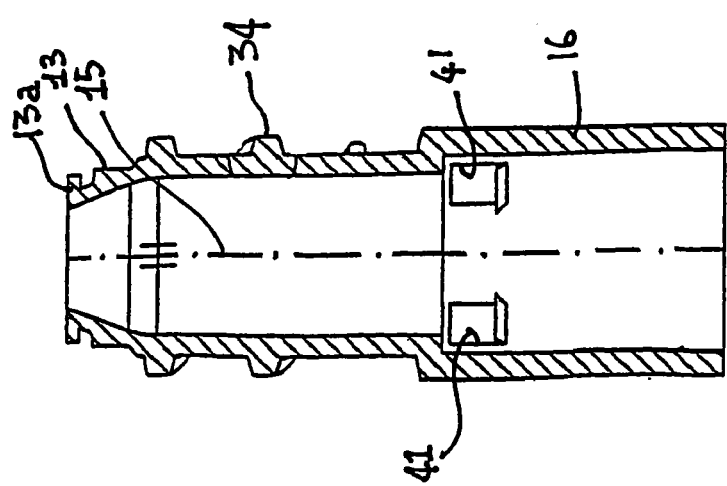

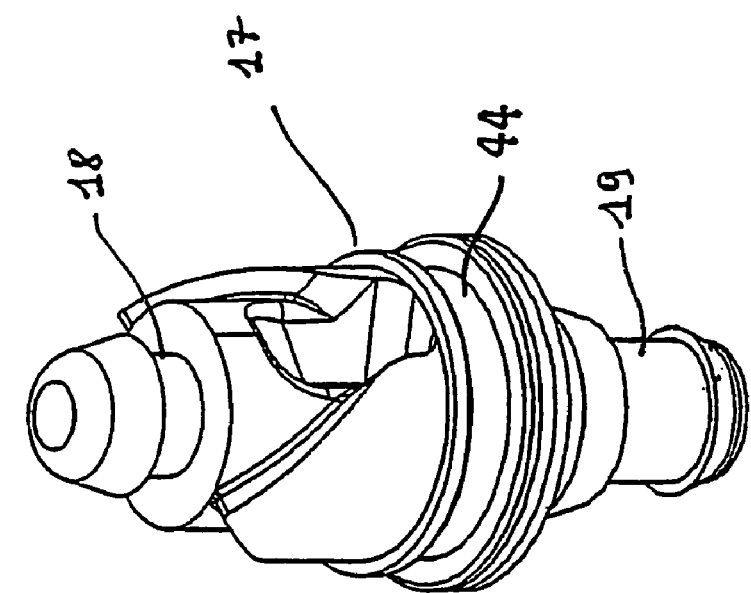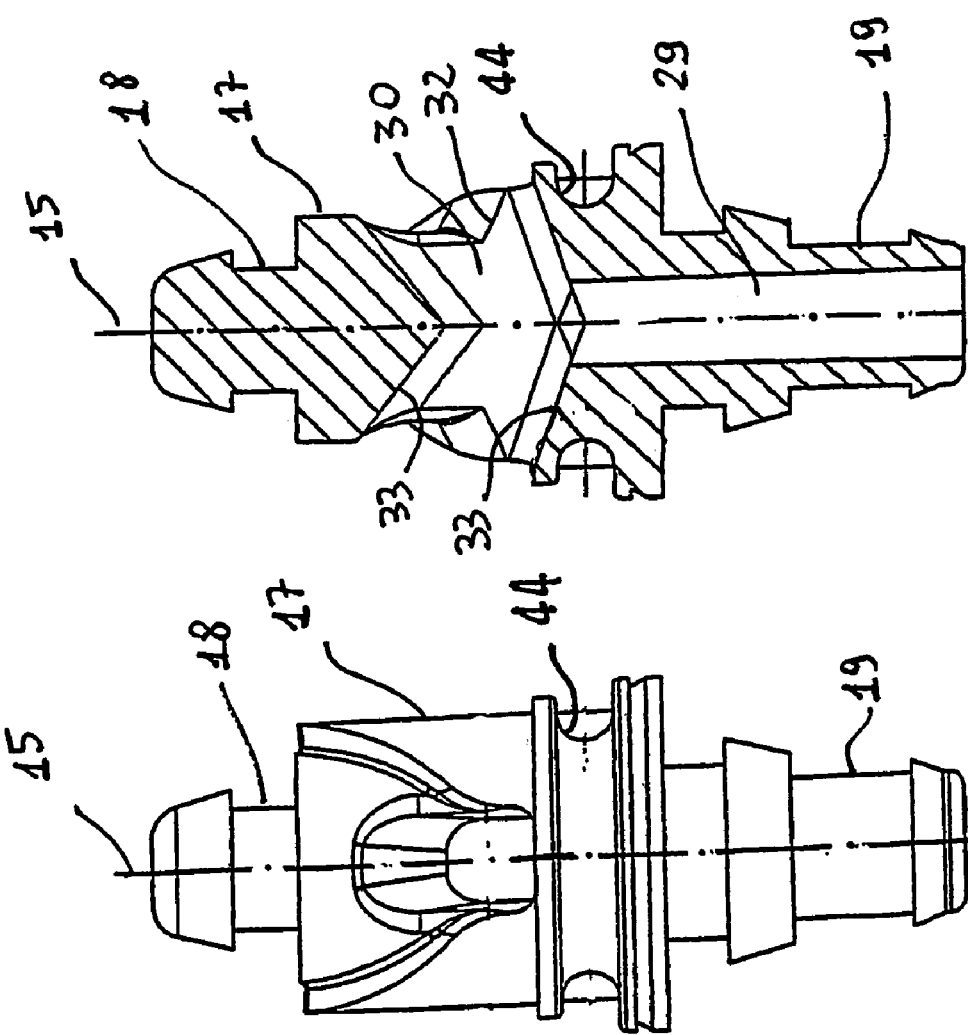
FIG. 16
FIG. 14
FIG. 15

CONNECTION ELEMENT AND CONNECTING DEVICE FOR TUBES

BACKGROUND OF THE INVENTION

The present invention relates to a connection element and a connecting device for tubes for medical use.

As is well known, in the medical field it is often necessary to set up fluid communication between pipes designed to carry liquids.

At the present time, to create a mechanical connection between consecutive terminal portions of two tubes, use may be made of connector elements attachable to the mutually opposing ends of the two tubes to be connected. Each connector element comprises a first portion that attaches onto the terminal portion of the respective tube, and a second portion designed for removable engagement on the other connector element. The mechanical connection between the two connectors is typically provided by threaded or bayonet couplings, Luer connections and the like.

It is however clear that connector devices described above can only provide a mechanical connection between the two terminal portions of tube and, if necessary, ensure the necessary fluidtightness.

There are however medical applications in which it is required to be able easily to create the mechanical connection between the two tubes that are to be joined up, but also to control the flow passing through the connected tubes. More specifically, if two fluid-transport lines are to be connected to each other, it is often necessary to stop the flow when the two lines are disconnected and allow the flow of fluid to resume immediately the two lines are properly connected.

With reference for example to peritoneal dialysis, there is typically a need to set up a connection between a line attached to the patient, in fluid communication with the interior of the peritoneum, and at least one infusion/drainage line designed to carry fluids to or from the patient's peritoneum.

To this end, if it is wished to use the connectors described above, the patient or an operator can make the physical connection between the line attached to the patient and a terminal portion of the infusion/evacuation line.

For the system to work properly, the infusion/evacuation lines and the tube connected to the patient must each have clamps or flow-prevention members, typically positioned in the vicinity of the terminal portion of the respective tube and capable of being adjusted from an open condition, in which they do not act on their respective tube, and a closed condition, in which they squeeze the tube so that the flow of fluid through the latter is stopped. In other words, the fixed line connected to the patient's peritoneum and the infusion/evacuation line must be fitted with suitable means capable of preventing the fluid leaking out until the operator has connected the two lines together.

From the operational point of view, a precise procedure must be followed when carrying out any connection operation between the infusion/evacuation line and the portion of tube connected to the patient: first of all any closure members situated at the end of each connector must be removed, and then the mechanical connection must be made between the line connected to the patient and the infusion/evacuation line, and finally the clamps must be opened.

From the above description is clear that a great deal of manipulation by the hands is required to make and break the connection. This is due to the structure of the connectors and to the fact that the connectors and flow-prevention elements (clamps) employed are functionally independent of each other.

In addition to this, the solution described can be seen to be favourable in certain situations to bacterial growth.

Specifically, the section of line extending between each flow-prevention clamp and the end of the tube is only wetted by the flow during use. Although, theoretically, at the beginning and end of each treatment this section undergoes a washing and disinfecting procedure, it is obvious that great care is required on the part of the user to reduce the possibility of bacterial growth.

In view of the limitations of the connectors described above, other technical approaches have been developed in the past and these will now be briefly described.

U.S. Pat. No. 5,743,892 discloses a connection system for peritoneal dialysis comprising a first connector on a tube attachable to patient and a second connector attached to an infusion/drainage tube. During coupling of the two connectors, an annular element on the second connector disinfects a coupling portion of the first connector. The connectors also include a clamp which can be operated by hand to prevent or regulate the flow through said connectors.

This approach fails to solve the problem of the complex hand movements required, as the functions of mechanical connection and flow prevention are separate. Also, the clamps of each connector operate at a distance from the free end of said connector, only partly solving the problems of bacterial growth outlined above.

Another known approach, designed to improve the problems of connecting and disconnecting a peritoneal dialysis line, is disclosed in patent EP 0 724 464. This document illustrates a connection system comprising a first connection element connected to an infusion/drainage line and a second connection element connected to a fixed line in fluid communication with the peritoneum of a patient. When the two connectors are being mechanically coupled, a pusher on the first connector angularly displaces a pivoting shutter on the second connector. In this way the lines connected to the first and second connectors are placed in fluid communication.

Besides the evident structural and constructional complication, the approach described above can only work if the second connector has a clamp to ensure that the flow cannot get through the second connector when the first is disengaged. In fact the second connector of the system described in EP 0 724 464 has a clamp on a section at a distance from the inlet-outlet section of said connector. In practice, the connection system described above evidences substantially the same limitations as the other known solutions.

There are also technical solutions that use a connector element defining in its interior a fluid passage between an inlet opening and an outlet opening and capable of performing the functions of both mechanical compression and, at the same time, flow regulation. In particular, U.S. Pat. No. 5,730,418 discloses a connector comprising a resilient shut-off element able to move from an open condition, in which it lets the fluid through, to a closed condition, in which an active portion of the resilient element positions itself flush with an inlet opening of the connector to stop the flow as desired. The solution described in U.S. Pat. No. 5,730,418 requires however that the internal deformable element has a highly asymmetric structure, in such a way as to fold up upon itself when a male element is inserted through the access opening. Despite the fact that this configuration allows flow to be opened when desired, it also defines a tortuous path for the flow of fluid through the connector, with obvious areas where the fluid can stagnate, and significant pressure losses, especially at high flowrates.

It should be pointed out that the presence of a "clean" flow with few or no areas of stagnation helps to improve the quality of the flow in fluid dynamic terms and helps to reduce the possibility of bacterial developing and growing.

SUMMARY OF THE INVENTION

In the light of the foregoing, the object of the present invention is to provide a connection element for tubes for medical use, that will make it possible more easily to mechanically connect two terminal tube portions and prevent/allow flow through said tubes. In particular it is a fundamental object of the invention to provide a novel connection element capable of combining the functions of mechanical connection and flow regulation and which at the same time is capable of allowing a flow with few or no areas of stagnation, and with reduced pressure losses even at relatively high flow rates, so that there is little encouragement to the growth of bacterial contamination.

Another object of the invention is to provide a connector device that will be particularly useful in peritoneal dialysis as a connection element between an infusion/drainage line and an access line connected to the peritoneum of a patient.

Lastly, it is an object of the invention to provide a connector device having a simple structure.

These and other objects, which will become apparent in the course of the following description, are largely achieved with a connector element for tubes for medical use and with a line for peritoneal dialysis using this connector element, in accordance with one or more of the accompanying claims.

Other characteristic advantages will be made apparent by a detailed description of a preferred, but not exclusive embodiment of a connector for tubes for medical use in accordance with the present invention.

BRIEF DESCRIPTION OF THE DRAWINGS

This description will be given with the aid of the attached drawings, which are supplied by way of guidance only and are therefore not limiting. In the figures:

FIG. 1 is a longitudinal view of a connecting device for tubes for medical use using connector elements in accordance with the present invention;

FIG. 2 is a section on II-II as marked in FIG. 1;

FIG. 3 is a view on III-III as marked in FIG. 2;

FIG. 4 is a section on IV-IV as marked in FIG. 3;

FIG. 10 is a schematic longitudinal section through a connector element in accordance with a last variant of the present invention;

FIG. 11 is a longitudinal view of an outer body part of the connector element of FIG. 10;

FIG. 12 is a cross section according to XII-XII of FIG. 11;

FIG. 13 is a longitudinal section according to XIII-XIII of FIG. 11;

FIG. 14 is a longitudinal section of an inner core which is part of the connector element of FIG. 10;

FIG. 15 is a longitudinal view of the inner core of FIG. 14;

FIG. 16 is a perspective view of the inner core of FIG. 14.

DETAILED DESCRIPTION

With reference to the attached figures, reference number 1 is a general reference for a connecting device for tubes for medical use in accordance with the present invention.

Figure 5:
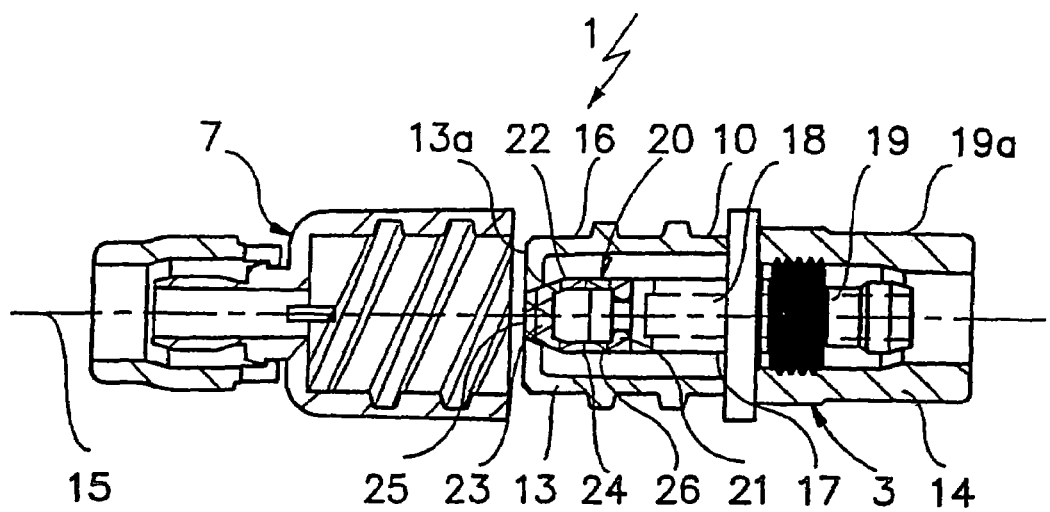
FIG. 5 is a longitudinal section through a connecting device for tubes for medical use using connector elements in accordance with a variant of the present invention.
Figure 6:
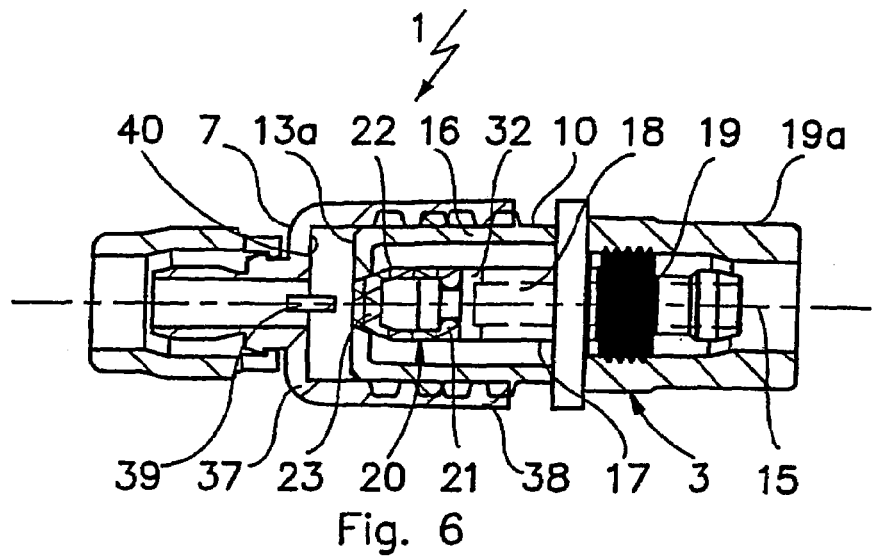
FIG. 6 is a section similar to FIG. 5 in which the connector elements are partly connected together.
Figure 7:
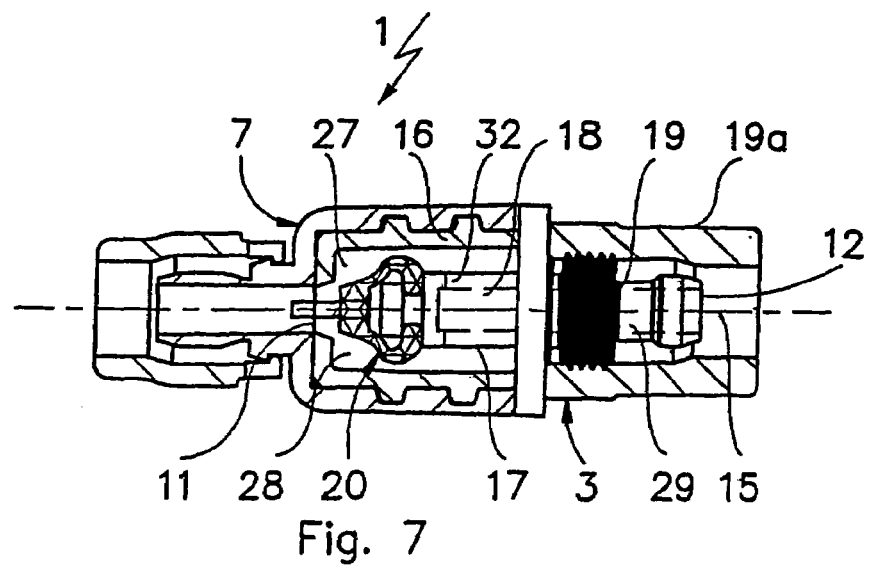
FIG. 7 is a section similar to FIG. 5 in which the connector elements are connected together to define a condition of fluid passage.
Figure 8:
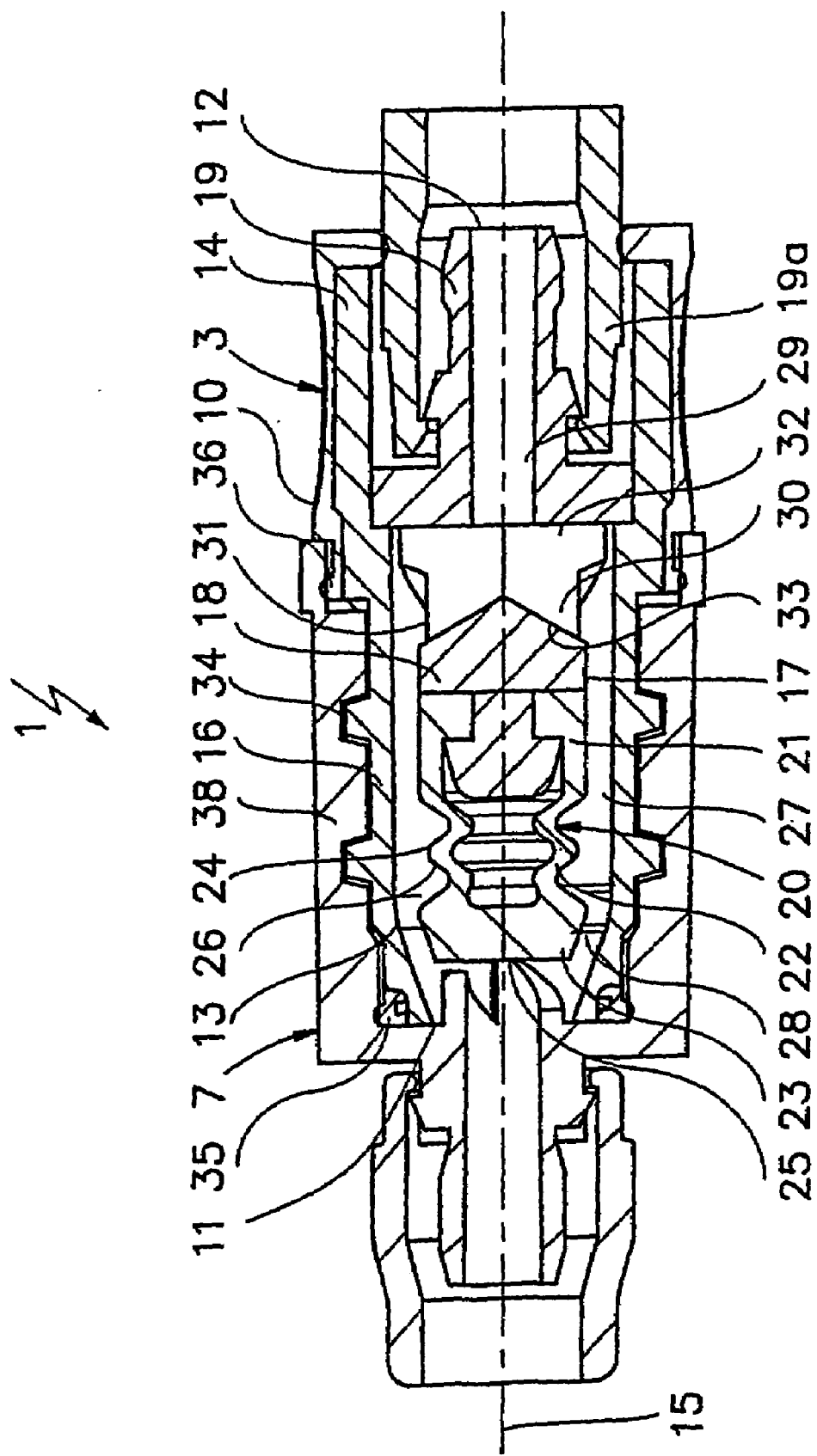
FIG. 8 is a longitudinal section through a connecting device for tubes for medical use using connector elements in accordance with another variant of the present invention.
Figure 9:
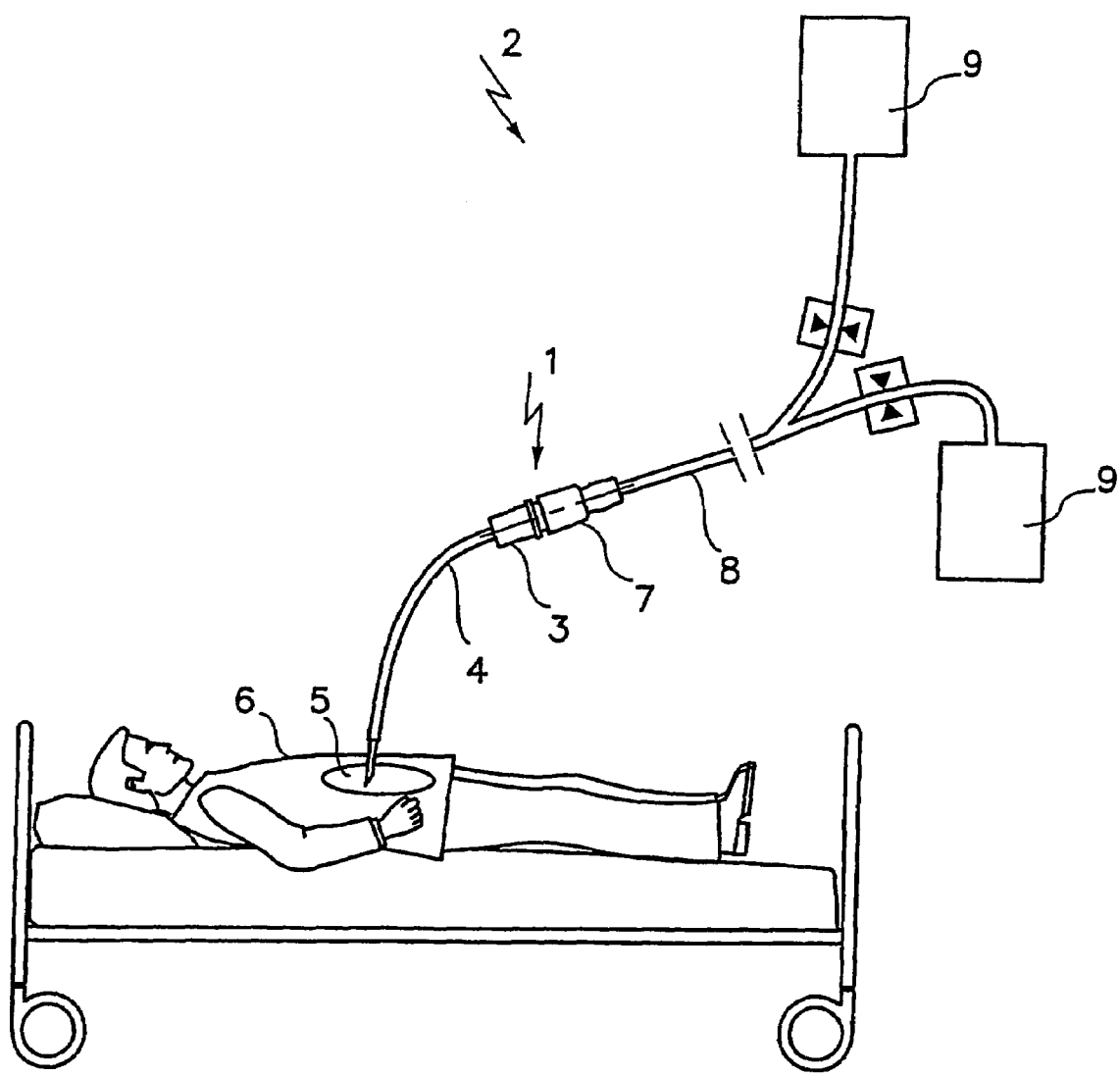
FIG. 9 shows an application of the present device to a line for peritoneal dialysis.

In particular, FIG. 9 shows an application of the device 1 to a line for peritoneal dialysis, bearing the general reference number 2. In greater detail, the device 1 comprises a connection element 3 attached to the end of a tube 4, the latter being designed to be placed in fluid communication with the peritoneal cavity 5 of a patient 6. The device 1 also includes an auxiliary connection element 7 attached to the end of another tube 8 connected to two or more containers 9 that may be used for infusing fresh fluid into the peritoneal cavity or evacuating fluid from the same peritoneal cavity. The two connector elements 3 and 7 are designed to be connected mechanically together, when in use, to allow fluid communication between the pipes 4 and 8 described above, allowing infusion or, alternatively, evacuation of fluid from the peritoneal cavity. The pipe 8 connected to the auxiliary connection element 7 can be placed in fluid communication with one or more bags of infusion fluid, using conventional valves capable of selective connection of the tube to the bag or container in question during the treatment. The connection element 3 attached to the end of the pipe 4 comprises a main body 10 defining an internal fluid passage between a first opening 11 and a second opening 12, which are at a distance from each other. More precisely, the main body 10 has an axial-symmetric configuration and comprises a distal end 13 in which is defined a leading edge 13a defining said first opening 11. The connector element 3 also includes a proximal end 14 where the second opening 12 is defined, this opening being axially opposed to the first opening on a longitudinal axis of symmetry 15 of the main body.

The main body consists structurally of an outer tubular body 16, inside which there operates a core 17 (only schematically represented in FIG. 10) situated predominantly at the proximal end of the connector element and extending coaxially relative to the tubular body.

As FIGS. 2 and 4 in particular show, the core in turn has an attachment portion 18 oriented towards said inlet opening and a tubular expansion 19 oriented towards said outlet opening. The attachment portion is housed in an internal position with respect to the tubular body, while the tubular expansion may also extend part of the way out of the tubular body 10 and is designed to be secured to the pipe 4 communicating with the peritoneum of the patient. In particular, in the examples illustrated here, a terminal portion of the pipe 4 is fixed between the tubular expansion 19 and a locking ring 19a which snap-locks or screws onto said tubular expansion. Other ways of locking the pipe 4 to the connection element 3 may also be used depending on requirements.

The connection element 3 also has a shut-off element 20 made entirely of elastically deformable material with little or no elastic memory; the shut-off element 20 is at least partially housed inside the main body, to allow or prevent, as required, fluid communication between said first and second openings of the main body. In the examples illustrated the shut-off element 20 is housed inside the tubular body and has a fixing portion 21 engaged on the main body 10. More precisely the fixing portion 21 defines at least one annular portion that engages in a mating undercut on the attachment portion 18 of the core 17. The shut-off element also has an intermediate portion 22 that continues from the fixing portion. The intermediate portion of the shut-off element is axially deformable and extends towards the first opening. Finally, the shut-off element has a sealing portion 23 continuing on from the intermediate portion and designed to be moved as required, at least between a first operating condition, in which the sealing portion closes off the first opening 11 and prevents fluid communication between the first and second openings 11, 12, and a second operating condition in which the sealing portion is positioned within the main body to allow fluid communication between said first and second openings 11, 12. At least the intermediate portion of the shut-off element has a longitudinal axis of symmetry coinciding with the longitudinal axis of symmetry of the main body 10, and is designed to deform symmetrically during the move from said first condition to said second condition. In the embodiments illustrated, the shut-off element and the main body, and therefore the entire connection element, have a symmetrical structure with respect to the abovementioned longitudinal axis of symmetry. It should be noted that, when in said closed condition, the sealing portion 23 of the shut-off element 20 is against the leading edge 13a of the main body defining said first opening. In particular, the sealing portion comes exactly flush with the leading edge, to give the connector element a continuous distal surface, without difficult-to-clean recesses in which concentrations of bacteria could hide. In practice, in closed conditions, the total distal surface of the connection element is given by the complementarity of the leading edge and the sealing portion which define a perfectly smooth surface, flat or convex and without cavities.

Turning now to a detailed description of the shut-off element, the latter has an outer surface 24 comprising a transverse end surface 25 and a lateral surface 26, each being intended to be in contact with a fluid passing through the connector when the shut-off element is in said open condition. The lateral surface of the shut-off element and the inner surface of the main body are both surfaces of revolution about said longitudinal axis of symmetry 15 of the connector. In this way the main body defines, in combination with said shut-off element, a fluid channel 27 with an axial-symmetric configuration with respect to said longitudinal axis of symmetry of the shut-off element. It should be observed that, owing to the structure of the shut-off element 20, the channel always has an axial-symmetric configuration, whether the closed or open or during the transition from the open to the closed condition. The fluid channel 27 comprises in particular a distal portion 28 extending between the shut-off element and the outer body; a proximal portion 29 extending inside the tubular expansion of the core; and a joining portion 30 between said distal and proximal portions of said channel, this portion leading through an intermediate section 31 of the core between said tubular expansion and said attachment portion. As the enclosed figures show, the distal portion 28 of the fluid channel takes up more radial room than the proximal portion; in order to connect the distal portion to the proximal portion of the channel, the joining portion 30 comprises openings 32 through said intermediate portion, which converge progressively together as they approach said proximal portion of the channel. The converging openings 32 are distributed symmetrically and, in the examples shown in FIGS. 1-4, FIG. 8, and FIGS. 10-16 are defined by walls 33 which are inclined with respect to said longitudinal axis of symmetry 15 to allow fluid to flow through the connector with virtually no stagnation. In the example illustrated in FIGS. 1 to 4, the intermediate portion 22 of the shut-off element is bellows-shaped and is therefore capable of deforming axially, having roughly constant radial dimension along its axial length and more or less invariable radial dimension during the deformation. Consequently, the distal portion 28 of the fluid channel also has an approximately constant annular cross section under all operating conditions of the connector.

The connection element comprises means 34 for removably coupling the main body to an auxiliary connection element connectable to a second tube. These means are defined for example by a thread, or a suitable forced-coupling portion, or a bayonet coupling or some other coupling element capable of ensuring the mutual engagement and disengagement of two connection elements. The connection element 3 of FIG. 8 comprises a first annular sealing element 35 engaged on the outside of said main body on said distal surface, and a second annular sealing element 36 engaged on the outside of the main body and at an axial distance from the first sealing element. The coupling means 34 operate between said first and second sealing elements. It should be observed that the presence and the particular arrangement of the first annular element 36 ensure fluidtightness even during the transitional movement when the auxiliary connector element 7 is being coupled. As already mentioned, the device 1 comprises an auxiliary connection element connectable to an end portion of a second tube and designed to be removably engaged on the main body of said connector element to give fluid communication between the first and second tubes. This auxiliary element in turn possesses a main body 37 defining at least one fluid passage and having a coupling portion 38 that mates with said outer body and a male element 39 emerging from a base 40 of said coupling portion. The male element is designed to push the sealing portion of the shut-off member from said closed condition to said open condition, as a result of the connector element 3 engaging with the element 7. The male element also has an axial-symmetric structure with respect to said axis 15 and is collar-shaped with symmetrically opposed lateral windows for the fluids to pass through.

A last embodiment of a connection element 3 according to the present invention is shown in FIGS. 10-16. In FIGS. 10-16, the same reference numbers have been used to identify features in common with the connection element 3 according to the first embodiment of FIGS. 1-4. Therefore, to avoid repetitions, here below only the features which distinguish the embodiment of FIGS. 10-16 from the connection element of FIGS. 1-4 will be described in detail.

The connection element 3 of comprises an outer body 16 having at least a passage 41 on its lateral surface. In the embodiment shown, four small windows symmetrically positioned with respect to axis 15 are provided. The outer body 16 externally carries a grip body 42 having protrusions 43 passing through said passages 41 and joining the outer body 16 to the core 17. The core 17 presents an annular recess 44 on its lateral surface engaging with said protrusion(s) 43. In other words, the protrusions 43 are integral in one piece with the grip body 42 and pass through the four windows 41 thereby engaging the annular recess 44 and creating an undercut 45 with respect to the outer body 16. From an assembling point of view, once the outer body 16 and the core 17 have been prepared, then the core is inserted and coaxially positioned inside the outer body; subsequently, the grip body 42 is moulded over the outer body 16 for creating the protrusions 43 which go through said passage(s) 41 and engage said recess 44 thereby axially connecting the core 17 to the outer body 16.

Due to the moulding process, the grip body 42 is fixed to the outer body 16 and contemporaneously linked to the core 17 thereby obtaining in just one step both the mechanical connection of body 16 and core 17 and the definition of a portion adapted to be handled by the user. Note that normally the grip body 42 is in a material different (for instance plastics softer then the plastics used for core 17 and body 16) from the materials used for manufacturing the core and the outer body 16. The grip body is shaped as a tubular sleeve engaged on a proximal portion of the main body. Also in this last embodiment a first annular sealing element 35 is engaged on the outside of said main body on the distal surface, and a second annular sealing element 36 is defined by a terminal edge of the grip body at an axial distance from the first sealing element. Again, the coupling means 34, such as a thread or a bayonet coupling or a snap fitting or a forced interference coupling or other convenient coupling, operate between said first and second sealing elements.

The invention claimed is:

1. A connection element for tubes for medical use, comprising:
    a main body defining at least one fluid passage between a first opening and a second opening, said second opening being positioned at a first distance from said first opening, said main body being configured to be attachable to the end of a first tube, and
    a shut-off element made of an elastically deformable material, said shut-off element being at least partly housed inside the main body, to allow or prevent fluid communication between said first and second openings of the main body, said shut-off element comprising:
        a fixing portion engaged on the main body;
        an intermediate portion extending from said fixing portion, said intermediate portion having a longitudinal axis of symmetry and being axially deformable;
        a sealing portion extending from the intermediate portion and configured to be moved, at least between a first operating condition, in which the sealing portion shuts off the first opening and prevents said fluid communication between the first and second openings, and a second operating condition in which the sealing portion is positioned at a second distance from the first opening to allow fluid communication between said first and second openings; and
        an outer surface having a transverse end surface and a lateral surface, said transverse end surface and said lateral surface being configured, in said second operating condition, to be swept by a fluid;
    at least said intermediate portion of the shut-off element being configured to deform symmetrically during the transition from said first operating condition to said second operating condition, said intermediate portion presenting a bellows shape to have constant radial dimension during axial deformation.

2. A connection element according to claim 1, wherein, in said first operating condition, the sealing portion of the shut-off element cooperates with a leading edge defining said first opening, said sealing portion being positioned level with the leading edge so that the connection element has a continuous distal surface.

3. A connection element according to claim 2, wherein, in said first operating condition, the sealing portion of the shut-off element is flush with said leading edge to define a distal surface of the connection element that is smooth and flat or slightly curved.

4. A connection element according to claim 1, wherein said lateral surface constitutes a surface of revolution about said longitudinal axis of symmetry.

5. A connection element according to claim 1, wherein the main body defines, in combination with said shut-off element, a fluid channel having an axial-symmetric configuration with respect to said longitudinal axis of symmetry of the shut-off element said intermediate portion.

6. A connection element according to claim 5, wherein the fluid channel has an axial-symmetric configuration with respect to said longitudinal axis of symmetry of said intermediate portion, both in said second operating condition and in said first operating condition.

7. A connection element according to claim 1, wherein said main body comprises:
    an outer body of essentially tubular configuration, and
    a core fixed to the outer body, said core having an attachment portion for the fixing portion of the shut-off element to engage with.

8. A connection element according to claim 7, wherein said core extends coaxially with the shut-off element in a radially inward position with respect to the outer body.

9. A connection element according to claim 8, wherein said core has a tubular expansion at an axially opposite end from said attachment portion and from said shut-off element.

10. A connection element according to claim 9, wherein the main body defines, in combination with said shut-off element, a fluid channel having an axial-symmetric configuration with respect to said longitudinal axis of symmetry of said intermediate portion, both in said second operating condition and in said first operating condition, the fluid channel comprising:
    a distal portion extending between said shut-off body and said outer body;
    a proximal portion extending inside said tubular expansion, and
    a joining portion between said distal and proximal portions of said fluid channel, extending through an intermediate section of the core between said tubular expansion and said attachment portion.

11. A connection element according to claim 10, wherein the distal portion of the fluid channel has a radial dimension greater than the proximal portion, said joining portion comprising openings formed on said intermediate section, said openings converging progressively towards said proximal portion of the fluid channel.

12. A connection element according to claim 11, wherein the openings formed on said intermediate section are formed in symmetrically opposing pairs with respect to said longitudinal axis of symmetry of said intermediate portion.

13. A connection element according to claim 10, wherein said tubular expansion is configured to be engaged to a terminal portion of the first tube.

14. A connection element according to claim 10, wherein the sealing portion, the intermediate portion, and the fixing portion are made of a single piece of elastomeric material.

15. A connection element according to claim 7, wherein a lateral surface of the outer body presents at least a through window, the outer body externally carrying a grip body having at least a radial protrusion passing through said through window and joining the external body to the core.

16. A connection element according to claim 15, wherein the core has a lateral surface, the lateral surface having a recess that engages said protrusion.

17. A connection element according to claim 16, wherein the recess is annular and said protrusion defines an undercut with respect to the outer body.

18. A connection element according to claim 15, wherein the lateral surface of the outer body presents a plurality of passages, the outer body externally carrying the grip body having a corresponding plurality of protrusions passing through said passages and joining the external body to the core.

19. An assembling process of a connecting element providing the connection element of claim 15; comprising the steps of:
preparing the outer body;
preparing the core;
positioning the core coaxially inside the outer body; and
moulding the grip body over the outer body for creating the protrusion extending through said passage, said protrusion engaging said recess thereby axially connecting the core to the outer body.

20. A connection element according to claim 1, further comprising means for removably coupling the main body to an auxiliary connection element connectable to a second tube.

21. A connection element according to claim 20, comprising a first annular sealing element engaged on a distal surface of the outside of said main body, and a second annular sealing element engaged on the outside of the main body at an axial distance from the first sealing element, said means for removably coupling being configured to operate between said first and second annular sealing elements.

22. A connection element according to claim 1, further comprising at least one first annular sealing element engaged on a distal surface of the outside of said main body.

23. A connection element according to claim 1, wherein said main body includes a rigid material.

24. A connecting device for tubes for medical use, comprising a connection element in accordance with claim 1.

25. A connecting device according to claim 24, comprising an auxiliary connection element connectable to a terminal portion of a second tube and configured to be engaged removably on the main body of said connection element to provide fluid communication between the first tube and the second tube.

26. A connecting device according to claim 25, wherein the auxiliary connection element comprises an auxiliary main body defining at least one auxiliary fluid passage and having a coupling portion that mates with said outer body and a male element emerging from a base of said coupling portion, said male element being configured to push said sealing portion of the shut-off member from said second operating condition to said first operating condition.

27. A connecting device according to claim 26, wherein the male element is of an axial-symmetric configuration with an axis of symmetry aligned with that of said shut-off element, when the connection element and auxiliary connection element are in mutual engagement.

28. A connecting device according to claim 26, wherein the male element comprises a collar with lateral ports arranged symmetrically with respect to said axis of symmetry, for a fluid to pass through.

29. A peritoneal dialysis line comprising:
at least one tube configured to be placed in communication with a peritoneum of a patient;
at least one second tube configured to be placed in communication with at least one container of a fluid to be infused into said peritoneum or with a container for draining a fluid coming from the peritoneum; and
a connecting device according to claim 24.

30. A tube for a peritoneal dialysis line, comprising at least one terminal portion fitted with a connection element in accordance with claim 1.

31. A connection element for tubes for medical use, comprising:
a main body defining at least one fluid passage between a first opening and a second opening, said second opening being positioned at a first distance from said first opening, said main body being configured to be attachable to an end of a first tube, said main body having an outer body of essentially tubular configuration and a core fixed to the outer body;
a shut-off element made of an elastically deformable material, said shut-off element being at least partly housed inside the main body, to allow or prevent fluid communication between said first and second openings of the main body, said shut-off element comprising:
a fixing portion engaged on the main body,
an intermediate portion extending from said fixing portion, said intermediate portion having a longitudinal axis of symmetry and being axially deformable, and
a sealing portion extending from the intermediate portion and configured to be moved, at least between a first operating condition, in which the sealing portion shuts off the first opening and prevents said fluid communication between the first and second openings, and a second operating condition in which the sealing portion is positioned at a second distance from the first opening to allow fluid communication between said first and second openings,
at least said intermediate portion of the shut-off element being configured to deform symmetrically during the transition from said first operating condition to said second operating condition,
said core of the main body extending coaxially with the shut-off element in a radially inward position with respect to said outer body, said core further having an attachment portion for the fixing portion of the shut-off element to engage with, and a tubular expansion at an axially opposite end from said attachment portion and from said shut-off element, and
said main body further defining, in combination with said shut-off element, a fluid channel having an axial-symmetric configuration with respect to said longitudinal axis of symmetry of the intermediate portion, both in said second operating condition and in said first operating condition, the fluid channel comprising:
a distal portion extending between said shut-off body and said outer body,
a proximal portion extending inside said tubular expansion, and
a joining portion between said distal and proximal portions of said fluid channel, said joining portion extending through an intermediate section of the core between said tubular expansion and said attachment portion, said distal portion having a radial dimension greater than the proximal portion, and said joining portion having openings formed on said intermediate section, said openings converging progressively towards said proximal portion of the fluid channel.

32. A connection element according to claim 31, wherein the openings formed on said intermediate section are formed in symmetrically opposing pairs with respect to said longitudinal axis of symmetry.

33. A connection element according to claim 31, wherein the intermediate portion of the shut-off element is configured to deform axially while maintaining a substantially constant radial dimension, so that said distal portion of the fluid channel has a substantially constant annular cross section.

34. A connection element according to claim 31, further comprising means for removably coupling the main body to an auxiliary connection element connectable to a second tube.

35. A connection element according to claim 34, comprising a first annular sealing element engaged on a distal surface of the outside of said main body, and a second annular sealing element engaged on the outside of the main body at an axial distance from the first sealing element, said coupling means operating between said first and second annular sealing elements.

36. A connection element according to claim 31, further comprising at least one first annular sealing element engaged on a distal surface of the outside of said main body.

37. A connection element according to claim 31, wherein said main body includes a rigid material.

38. A connection element according to claim 31, wherein said tubular expansion is configured to be engaged to a terminal portion of the first tube.

39. A connection element according to claim 31, wherein the sealing portion, the intermediate portion, and the fixing portion are made of a single piece of elastomeric material.

40. A connection element according to claim 31, wherein the outer body has a lateral surface, the lateral surface having a passage, the outer body externally carrying a grip body having at least a protrusion passing through said passage and joining the external body to the core.

41. A connection element according to claim 40, wherein a lateral surface of the core presents a recess engaging with said protrusion.

42. A connection element according to claim 41, wherein the recess is annular and said protrusion defines an undercut with respect to the outer body.

43. A connection element according to claim 40, wherein the lateral surface of the outer body presents a plurality of passages, the outer body externally carrying the grip body having a corresponding plurality of protrusions passing through said passages and joining the external body to the core.

44. An assembling process of a connecting element providing the connection element of claim 42; comprising the steps of:
preparing the outer body;
preparing the core;
positioning the core coaxially inside the outer body; and
moulding the grip body over the outer body for creating the protrusion extending through said passage, said protrusion engaging said recess thereby axially connecting the core to the outer body.

45. A connecting device for tubes for medical use, comprising a connection element in accordance with claim 31.

46. A connecting device according to claim 45, comprising an auxiliary connection element configured to connect to a terminal portion of a second tube and configured to be engaged removably on the main body of said connection element to provide fluid communication between the first tube and the second tube.

47. A connecting device according to claim 46, wherein the auxiliary connection element comprises an auxiliary main body defining at least one auxiliary fluid passage, the auxiliary main body having a coupling portion that mates with said outer body, and a male element emerging from a base of said coupling portion, said male element being configured to push said sealing portion of the shut-off member from said second operating condition to said first operating condition.

48. A connecting device according to claim 47, wherein the male element has an axial-symmetric configuration with an axis of symmetry aligned with the longitudinal axis of symmetry of said intermediate portion, when the connection element and the auxiliary connection element are in mutual engagement.

49. A connecting device according to claim 47, wherein the male element comprises a collar with lateral ports arranged symmetrically with respect to said axis of symmetry of the male element, for a fluid to pass through.

50. A peritoneal dialysis line comprising:
at least one tube configured to be placed in communication with a peritoneum of a patient;
at least one second tube configured to be placed in communication with at least one container of a fluid to be infused into said peritoneum or with a container for draining a fluid coming from the peritoneum; and
a connecting device according to claim 45.

51. A tube for a peritoneal dialysis line, comprising at least one terminal portion fitted with a connection element in accordance with claim 31.

52. A connection element for tubes for medical use, comprising:
a main body defining at least one fluid passage between a first opening and a second opening, said second opening being positioned at a first distance from said first opening, said main body being configured to be attachable to an end of a first tube, said main body having an outer body of essentially tubular configuration and a core fixed to and extending inside the outer body;
a shut-off element made of an elastically deformable material, said shut-off element being at least partly housed inside the main body, to allow or prevent fluid communication between said first and second openings of the main body, said shut-off element comprising:
a fixing portion engaged on the main body,
an intermediate portion extending from said fixing portion, said intermediate portion having a longitudinal axis of symmetry and being axially deformable, and
a sealing portion extending from the intermediate portion and configured to be moved, at least between a first operating condition, in which the sealing portion shuts off the first opening and prevents said fluid communication between the first and second openings, and a second operating condition in which the sealing portion is positioned at a second distance from the first opening to allow fluid communication between said first and second openings,
at least said intermediate portion of the shut-off element being configured to deform symmetrically during the transition from said first operating condition to said second operating condition,
said core of the main body having an attachment portion for the fixing portion of the shut-off element to engage with, and
said outer body of the main body having a lateral surface, the lateral surface presenting at least a through window, the outer body externally carrying a grip body having at least a radial protrusion passing through said through window, the radial protrusion engaging with an annular recess present on the core and joining the external body to the core of the main body.

53. A connection element according to claim 52, wherein said core extends coaxially with the shut-off element in a radially inward position with respect to the outer body.

54. A connection element according to claim 53, wherein said core has a tubular expansion at an axially opposite end from said attachment portion and from said shut-off element.

55. A connection element according to claim 54, wherein the main body defines, in combination with said shut-off element, a fluid channel having an axial-symmetric configuration with respect to said longitudinal axis of symmetry of the intermediate portion, both in said second operating condition and in said first operating condition, the fluid channel comprising:
- a distal portion extending between said shut-off body and said outer body;
- a proximal portion extending inside said tubular expansion, and
- a joining portion between said distal and proximal portions of said fluid channel, said joining portion extending through an intermediate section of the core between said tubular expansion and said attachment portion.

56. A connection element according to claim 55, wherein said tubular expansion is configured to be engaged to a terminal portion of the first tube.

57. A connection element according to claim 55, wherein the sealing portion, the intermediate portion, and the fixing portion are made of a single piece of elastomeric material.

58. A connection element according to claim 52, further comprising means for removably coupling the main body to an auxiliary connection element configured to be connected to a second tube.

59. A connection element according to claim 58, further comprising a first annular sealing element engaged on a distal surface of the outside of said main body, and a second annular sealing element engaged on the outside of the main body at an axial distance from the first sealing element, said coupling means operating between said first and second annular sealing elements.

60. A connection element according to claim 52, further comprising at least one first annular sealing element engaged on a distal surface of the outside of said main body.

61. A connection element according to claim 52, wherein said main body includes a rigid material.

62. A connection element according to claim 52, wherein the recess is annular and said protrusion defines an undercut with respect to the outer body.

63. A connection element according to claim 52, wherein a lateral surface of the outer body presents a plurality of through windows, the outer body externally carrying the grip body having a corresponding plurality of radial protrusions passing through said through windows and joining the external body to the core.

64. An assembling process of a connecting element providing the connection element of claim 52; comprising the steps of:
- preparing the outer body;
- preparing the core;
- positioning the core coaxially inside the outer body; and
- moulding the grip body over the outer body for creating the radial protrusion extending through said through window, said radial protrusion engaging said recess thereby axially connecting the core to the outer body.

65. A connecting device for tubes for medical use, comprising a connection element in accordance with claim 52.

66. A connecting device according to claim 65, comprising an auxiliary connection element configured to connect to a terminal portion of a second tube and configured to be engaged removably on the main body of said connection element to provide fluid communication between the first tube and second tube.

67. A connecting device according to claim 66, wherein the auxiliary connection element comprises an auxiliary main body defining at least one auxiliary fluid passage, the auxiliary main body having a coupling portion that mates with said outer body, and a male element emerging from a base of said coupling portion, said male element being configured to push said sealing portion of the shut-off member from said second operating condition to said first operating condition.

68. A connecting device according to claim 67, wherein the male element has an axial-symmetric configuration with an axis of symmetry aligned with the longitudinal axis of symmetry of said intermediate portion, when the connection element and the auxiliary connection element are in mutual engagement.

69. A connecting device according to claim 67, wherein the male element comprises a collar with lateral ports arranged symmetrically with respect to said axis of symmetry of said male element, for a fluid to pass through.

70. A peritoneal dialysis line comprising:
- at least one tube configured to be placed in communication with a peritoneum of a patient;
- at least one second tube configured to be placed in communication with at least one container of a fluid to be infused into said peritoneum or with a container for draining a fluid coming from the peritoneum; and
- a connecting device according to claim 65.

71. A tube for a peritoneal dialysis line, comprising at least one terminal portion fitted with a connection element in accordance with claim 52.

72. A connecting device for tubes for medical use, comprising a connection element having:
- a main body defining at least one fluid passage between a first opening and a second opening, said second opening being positioned at a first distance from said first opening, said main body being configured to be attachable to an end of a first tube;
- a shut-off element made of an elastically deformable material, said shut-off element being at least partly housed inside the main body, to allow or prevent fluid communication between said first and second openings of the main body, said shut-off element comprising:
  - a fixing portion engaged on the main body;
  - an intermediate portion extending from said fixing portion, said intermediate portion having a longitudinal axis of symmetry and being axially deformable; and
  - a sealing portion extending from the intermediate portion and configured to be moved, at least between a first operating condition, in which the sealing portion shuts off the first opening and prevents said fluid communication between the first and second openings, and a second operating condition in which the sealing portion is positioned at a second distance from the first opening to allow fluid communication between said first and second openings;
  - at least said intermediate portion of the shut-off element being configured to deform symmetrically during the transition from said first operating condition to said second operating condition;
- said connecting device further comprising an auxiliary connection element configured to connect to a terminal portion of a second tube and configured to be engaged removably on the main body of said connection element to provide fluid communication between the first tube and the second tube, said auxiliary connection element having an auxiliary main body defining at least one auxiliary fluid passage, said auxiliary main body having a coupling portion that mates with said outer body, and a male element emerging from a base of said coupling portion, said male element being configured to push said sealing portion of the shut-off member from said second operating condition to said first operating condition, said male element being having an axial-symmetric configuration with an axis of symmetry aligned with that of said intermediate portion, when the connection element and auxiliary connection element are in mutual engagement, said male element further having a collar with lateral ports arranged symmetrically with respect to said axis of symmetry of the male element, for a fluid to pass through.

73. A connection element according to claim 72, wherein said core extends coaxially with the shut-off element in a radially inward position with respect to the outer body.

74. A connection element according to claim 73, wherein said core has a tubular expansion at an axially opposite end from said attachment portion and from said shut-off element.

75. A connection element according to claim 74, wherein the main body defines, in combination with said shut-off element, a fluid channel having an axial-symmetric configuration with respect to said longitudinal axis of symmetry of the intermediate portion, both in said second operating condition and in said first operating condition; the fluid channel comprising:
 - a distal portion extending between said shut-off body and said outer body;
 - a proximal portion extending inside said tubular expansion, and
 - a joining portion between said distal and proximal portions of said fluid channel, extending through an intermediate section of the core between said tubular expansion and said attachment portion.

76. A connection element according to claim 75, wherein said tubular expansion is configured to be engaged to a terminal portion of the first tube.

77. A connection element according to claim 75, wherein the sealing portion, the intermediate portion, and the fixing portion are made of a single piece of elastomeric material.

78. A connection element according to claim 72, comprising means for removably coupling the main body to an auxiliary connection element configured to connect to a second tube.

79. A connection element according to claim 78, comprising a first annular sealing element engaged on a distal surface of the outside of said main body, and a second annular sealing element engaged on the outside of the main body at an axial distance from the first sealing element, said coupling means operating between said first and second annular sealing elements.

80. A connection element according to claim 72, comprising at least one first annular sealing element engaged on a distal surface of the outside of said main body.

81. A connection element according to claim 72, wherein said main body includes a rigid material.

82. A peritoneal dialysis line comprising:
 - at least one tube configured to be placed in communication with a peritoneum of a patient;
 - at least one second tube configured to be placed in communication with at least one container of a fluid to be infused into said peritoneum or with a container for draining a fluid coming from the peritoneum; and
 - a connecting device according to claim 72.

83. A tube for a peritoneal dialysis line, comprising at least one terminal portion fitted with a connection element in accordance with claim 72.

* * * * *

UNITED STATES PATENT AND TRADEMARK OFFICE
CERTIFICATE OF CORRECTION

PATENT NO. : 7,306,197 B2
APPLICATION NO. : 10/511391
DATED : December 11, 2007
INVENTOR(S) : Andrea Parrino et al.

It is certified that error appears in the above-identified patent and that said Letters Patent is hereby corrected as shown below:

In claim 19, column 9, lines 10-12, "An assembling process of a connecting element providing the connection element of claim 15; comprising the steps of:" should read --An assembling process of a connecting element comprising the steps of: providing the connection element of claim 15;--.

In claim 64, column 13, lines 48-50, "An assembling process of a connecting element providing the connection element of claim 52; comprising the steps of:" should read --An assembling process of a connecting element comprising the steps of: providing the connection element of claim 52;--.

Signed and Sealed this

Third Day of March, 2009

JOHN DOLL
*Acting Director of the United States Patent and Trademark Office*